United States Patent [19]

Stoltz

[11] 4,149,291
[45] Apr. 17, 1979

[54] POWER-OPERATED TOOTHBRUSH

[75] Inventor: Werner Stoltz, Friedrichsdorf, Fed. Rep. of Germany

[73] Assignee: Blendax-Werke R. Schneider GmbH & Co., Mainz, Fed. Rep. of Germany

[21] Appl. No.: 857,030

[22] Filed: Dec. 2, 1977

Related U.S. Application Data

[63] Continuation-in-part of Ser. No. 772,446, Feb. 28, 1977, abandoned.

[30] Foreign Application Priority Data

Feb. 26, 1976 [DE] Fed. Rep. of Germany ....... 2607820

[51] Int. Cl.² ............................................. A46B 13/02
[52] U.S. Cl. .................................................. 15/22 R
[58] Field of Search ................. 15/22 R, 22 A, 22 C; 128/45-47, 62 A

[56] References Cited

U.S. PATENT DOCUMENTS

| | | | |
|---|---|---|---|
| 3,133,297 | 5/1964 | Gerber et al. | 15/22 R |
| 3,183,538 | 5/1965 | Hubner | 15/22 R |
| 3,365,963 | 1/1968 | Happe | 15/22 R X |
| 3,538,530 | 11/1970 | Stemme | 15/22 R |
| 3,945,076 | 3/1976 | Sung | 15/22 R |

Primary Examiner—Edward L. Roberts
Attorney, Agent, or Firm—Connolly and Hutz

[57] ABSTRACT

An electrically powered toothbrush with an eliptical brushing motion comprising a motor-operated rotating output drive and a disk rotatably mounted thereon, said disk having at least one eccentric funnel-shaped orifice which serves as an end bearing for a flexible direct drive shaft, a direct output shaft having one end bearing on said funnel-shaped orifice and the opposite end constructed as a holder for a brush, a second bearing for said shaft being located at a point between the two shaft ends, said output shaft having rigidity in one plane of the axis of rotation and flexibility in a perpendicular plane whereby an eliptical brush rotation is achieved as a result of tooth counterpressure again the brush, and a housing.

8 Claims, 10 Drawing Figures

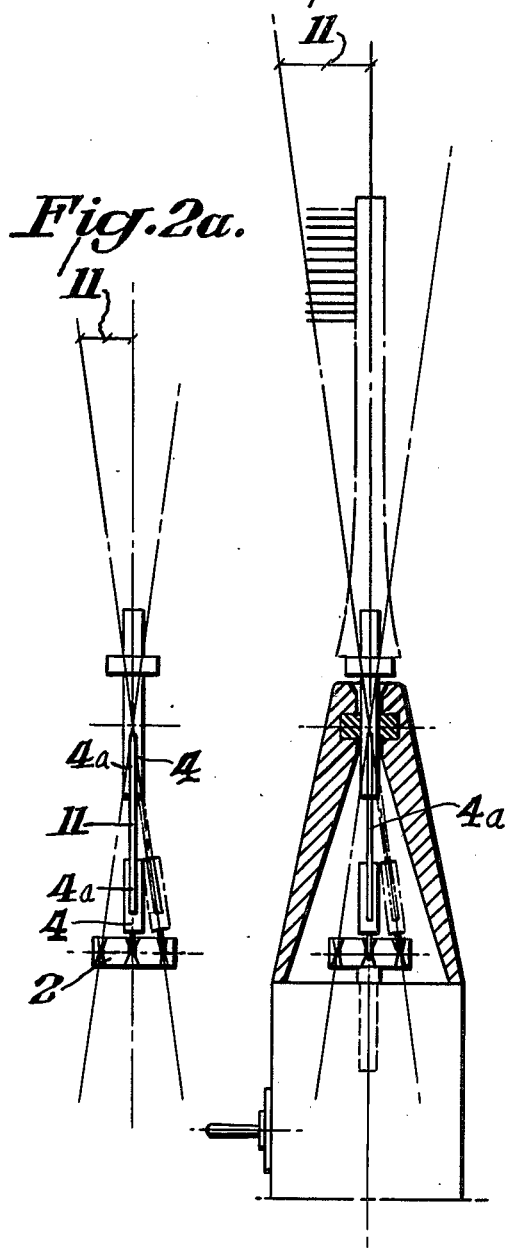
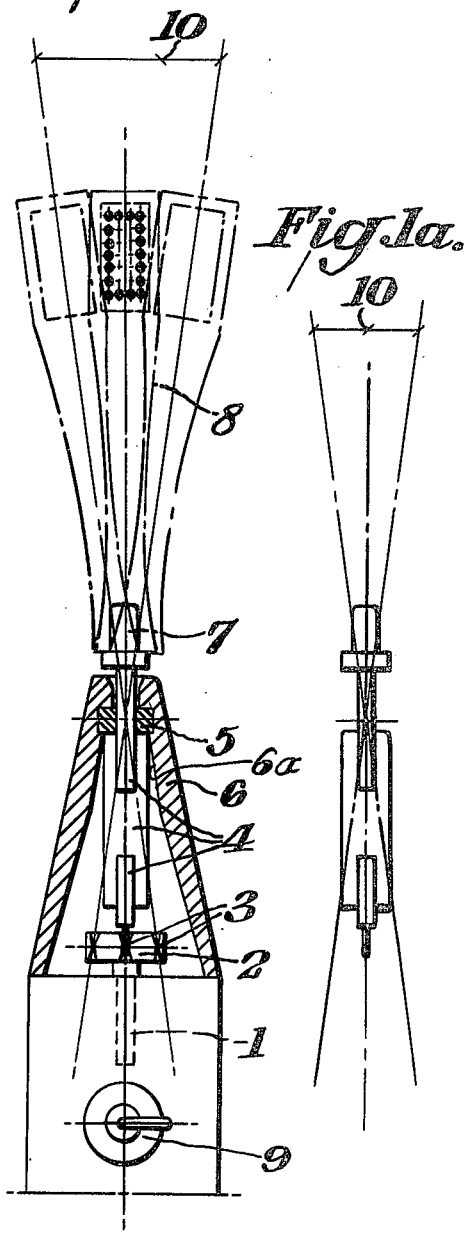
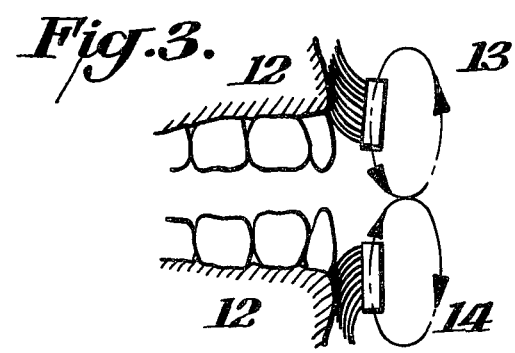
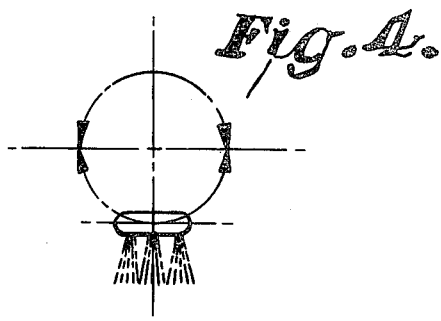

POWER-OPERATED TOOTHBRUSH

CROSS REFERENCE TO RELATED APPLICATION

This application is a continuation-in-part of my copending application Ser. No. 772,446 filed Feb. 28, 1977, now abandoned.

BACKGROUND OF THE INVENTION

Toothbrushes with an electrical or mechanical drive have been known for a long time. None of the toothbrushes of this type presently on the market, however, fulfill the requirement of cleaning the teeth having interdental spaces and periodontal pockets. In the usually known power-operated toothbrushes, which execute an oscillating cleaning movement, there exists the danger that food residues and other dental impurities may be brushed into the interdental spaces, into the pockets and also into the gums.

In has already been suggested to eliminate these drawbacks by the use of power-operated toothbrushes, rotating by their axis. Even toothbrushes with complicated crank systems already belong to the state of the art. Power-operated toothbrushes of this type, however, could previously, not succeed because their assembly was too complicated and thus too unwieldy and since they were also too expensive in manufacture. Also such brushes could not be used, particularly with respect to the rotating brushes, because of the possible danger of injury to the mucous membrane of the mouth on the inside of the cheeks and lips.

BRIEF DESCRIPTION OF THE DRAWINGS

FIG. 1 is a fragmentary sectional elevation of a power-operated toothbrush embodying the present invention as seen from the front of the brush bristles;

FIG. 1a. shows the output shaft 4 in a front view with schematically illustrated support and non-flexible angular freedom;

FIG. 2 is a view similar to FIG. 1 but in side elevation and shows the cross-position of flat spring 4a and its flexible curvature resulting from counterpressure of the teeth again the brush;

FIG. 2a is a side elevation of the output shaft shown in FIG. 1a with rotating disk 2 illustrated and showing flexible angular freedom as in FIG. 2;

FIG. 3 illustrates the eliptical teeth cleaning and brushing movement of a toothbrush embodying the present invention resulting from counterpressure of the brush head on the teeth;

FIG. 4 illustrates the motion of the brush head without counterpressure from the teeth;

DETAILED DISCLOSURE

The object of the present invention is to provide a power-operated toothbrush, which fulfulls the requirement of dental medicine of executing the brush movement from the gums out by means of its rotating and elliptic movement shown in FIG. 3, yet does not have the above-demonstrated drawbacks of the known brushes.

Figure 7:
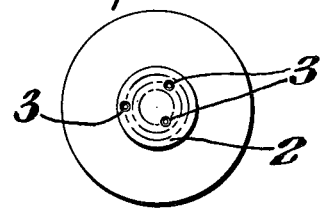
FIG. 7 is a top plan view of the rotating disk 2 and drive output housing shown in FIGS. 1, 2 and 5.

This problem is solved in such manner that on the rotating motor controlled drive shaft 1 of a power-operated toothbrush, there is situated a concentrically or eccentrically mounted disk 2 or the end of the drive shaft 1 is constructed as such a disk. In the disk there are situated one or more eccentric funnel-shaped orifices or bores 3 as shown in FIG. 7 which serve as end bearings for the accommodation of a direct drive shaft 4 whose opposed bearing is arranged in the frustoconical-shaped housing 6 of the toothbrush as shown in FIGS. 1, 2, 5 and 6 and whose end is constructed directly as a holder 7 for the slip-on brush 8. Inside wall 6a of housing 6 provides a limiting seat for flat spring 4a of output shaft 4.

Between the two shaft ends is situated a ball end and the accommodation for a flexible support 5 whose support or attachment is mounted nearly axially to the disk 2 attached on the rotating output shaft 1 in the housing 6 of the brush.

From this bearing, all axial forces are picked up, so that the stated disk is not axially loaded.

On the ball end or on the flexible bearing 5, the drive shaft 4 is locked in position in such a manner that it cannot turn axially.

Figure 6:
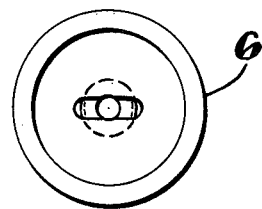
FIG. 6 is a bottom plan view of the frustoconical shaped housing 6 shown in FIGS. 1, 2 and 5.
Figure 5:
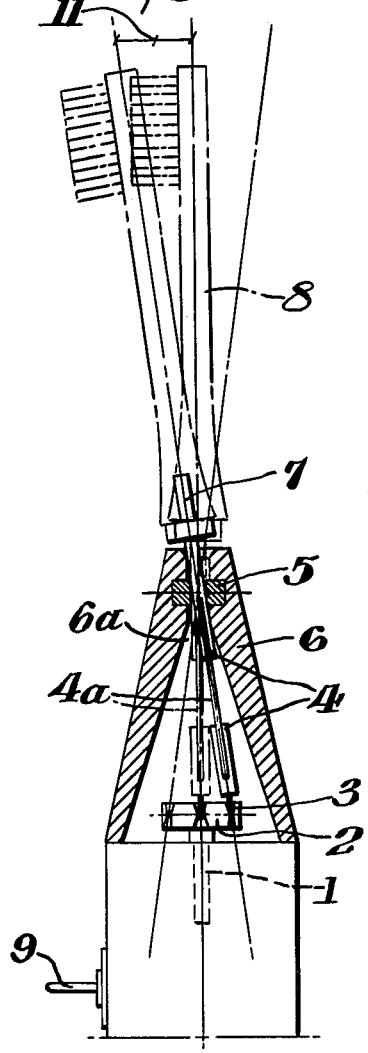
FIG. 5 is a view similar to FIG. 2 showing movement of the brush.
Figure 8:
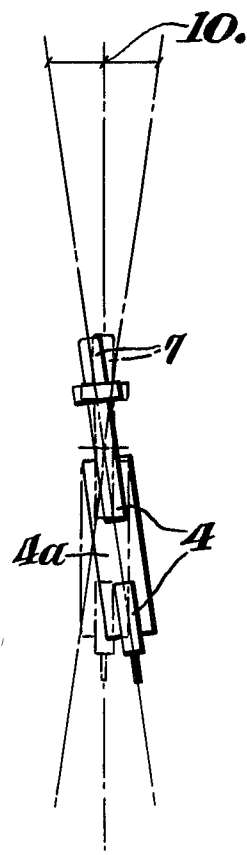
FIG. 8 is a view similar to FIG. 1a illustrating the movement of output shaft 4.

The transmission of the oscillation to the slip-on brush occurs then in such manner that with the rotation of disk 2 attached to the output, the output shaft supported therein is set in oscillation, whose oscillating nodes are situated in the ball end and in the flexible bearing, respectively, and which are transmitted to the toothbrush holder thereby. As shown in FIGS. 1, 1a and 8, the non-flexible angular freedom stroke of the brush movement is shown by reference numeral 10 and as shown in FIGS. 2, 2a and 5, the flexible angular freedom stroke affected by teeth counterpressure on the brush head is shown by reference numeral 11.

The output shaft 1 can be shaped in the form of a spring or may be connected between its bearing points, e.g. by means of a flat spring 4a or in similar manner with the bearing parts; e.g. by means of pivot cone and ball end.

The spring action suspension can also be mounted outside the toothbrush housing, for example between ball end and toothbrush attachment on the drive shaft. Preferably the spring action suspension of the output shaft is designed as a flat spring, which has the following advantage:

The oscillation stroke of the output shaft is not changed in the turning of the disk in the plane of the breadth of the flat spring in the absence of flexibility in this plane and consequently is fully retransmitted as the brush direction stroke to the brush attachment, whereas the oscillation stroke perpendicular to this plane is fully flexible due to the narrow side of the flat spring, and in this manner the pressure of the toothbrush against the gums and teeth and the brushing out may be controlled at will from soft to hard depending on the pressure applied by the user.

A particularly preferred embodiment of the inventively power-operated toothbrush has a reversing switch 9 by means of which the direction of rotation of the rotating disk may be changed and opposite brushing directions may be achieved as shown by 13 and 14 in FIG. 3. This reversing switch may be designed in a known manner as a toggle switch; a further embodiment is that of a slide or rotary switch which may be actuated by hand or by pressure against the teeth or lips upon slipping on the toothbrush, since it is important that, depending on application on the upper or lower jaw, the cleaning direction lead away from the gums in a given case as shown in FIG. 3.

It is possible to provide the switch with a variable resistance control to regulate the brushing speed and brushing power.

The inventively operated toothbrush is used in the following manner;

Upon turning on the reversing switch, there results at first a cone-shaped circulating rotation of the slip-on brush in the desired direction of rotation as shown in FIG. 4. The brush always points in one direction due to the locked-in position of the output shaft in the ball end or in the flexible bearing.

As shown in FIG. 3, the toothbrush is applied to the teeth, counterpressure of the toothbrush against the teeth and gums 12, the rotation is altered and transformed into an elliptical brush movement 13, 14 along the teeth, since the flexibility of the output shaft becomes fully effective and can be controlled by the counterpressure, so that there can be achieved a gentle application of the brush head for the brush stroke and a similar lifting for the return movement. The brush stroke is fully retained in the plane of the breadth of the flat spring and, with several eccentric bearing bores in the driven disk, may still be adjusted selectively in the stroke level of the output shaft. Thus it is advantageous to provide a disk with a plurality of bores having varying distances from the disk axis.

By the novel embodiment of the power-operated toothbrush, there results considerable technical progress. By the directionally adjustable teeth-cleaning procedure, the cleaning movement from the gums out (desired in dental medicine) can be achieved. Thus there is achieved an optimum cleaning of the interdental spaces and of the periodontal pockets. Use of the simple movement transmission by the output shaft which is variably flexible in different planes allows simple, expedient mass production of the apparatus.

These advantages cannot be achieved with rotating toothbrushes corresponding to the state of the art.

The drive of the novel teeth-cleaning apparatus can be achieved by means of a customary electric motor with a suitable rotational speed range. The energy source can be house current, a battery, a storage battery or also an electric circuit controlled optionally by a transformer.

What I claim is:

1. An electrically powered toothbrush with an eliptical brushing motion comprising a motor-operated rotating output drive and a disk rotatably mounted thereon, said disk having at least one eccentric funnel-shaped orifice which serves as an end bearing for a flexible direct drive shaft, a direct output shaft having one end bearing on said funnel-shaped orifice and the opposite end constructed as a holder for a brush, a second bearing for said shaft being located substantially axially to said disk at a point between the two shaft ends and locking the shaft in position to prevent rotation of the shaft, said output shaft having rigidity in one plane of the axis of rotation and flexibility in a perpendicular plane whereby an eliptical brush rotation is achieved as a result of tooth counterpressure again the brush, and a housing.

2. A toothbrush according to claim 1 wherein said output shaft is a flat spring.

3. A toothbrush according to claim 2 wherein said output shaft is a leaf spring which is supported and axially locked by said second bearing comprising a flexible material or a ball end whereby said spring cannot turn axially.

4. A toothbrush according to claim 1 wherein the disk is mounted eccentric to the rotating output drive.

5. A toothbrush according to claim 1 wherein the end of the rotating output drive itself serves as said disk.

6. A toothbrush according to claim 1 wherein the direction of rotation of the motor-operated rotating output drive is controlled by a reversing switch.

7. A toothbrush according to claim 6 wherein the switch is equiped with a variable resistor for adjusting the brushing speed.

8. A toothbrush according to claim 1 wherein said disk has a plurality of eccentric funnel-shaped bores each having a different distance from the disk axis.

* * * * *